United States Patent [19]

Baker

[11] Patent Number: 4,943,176

[45] Date of Patent: Jul. 24, 1990

[54] BODY ROLLER LIQUID APPLICATOR

[76] Inventor: Claudia Baker, 4441 Pacific Coast Hwy., Torrance, Calif. 90505

[21] Appl. No.: 352,152

[22] Filed: May 15, 1989

[51] Int. Cl.⁵ ............................................. B05C 17/02
[52] U.S. Cl. ..................................... 401/197; 132/320
[58] Field of Search ............... 401/197, 196, 208, 146, 401/207; 132/320

[56] References Cited

U.S. PATENT DOCUMENTS

| 596,090 | 12/1897 | Roux | 401/197 |
| 2,563,049 | 8/1951 | Liebelt | 401/197 |
| 3,877,823 | 4/1975 | Leland | 401/197 |

FOREIGN PATENT DOCUMENTS 862862  1/1953  Fed. Rep. of Germany ...... 401/197

Primary Examiner—Richard J. Johnson
Attorney, Agent, or Firm—William H. Maxwell

[57] ABSTRACT

A roller liquid applicator wherein restrictedly rotatable cylinder members store liquid and with bearing arms with an extended grip to reach all areas of a person's body, relative rotation of the members controlling the discharge of liquid through a valve and distributed by a manifold into a sleeve for application by rolling onto the person's body.

13 Claims, 2 Drawing Sheets

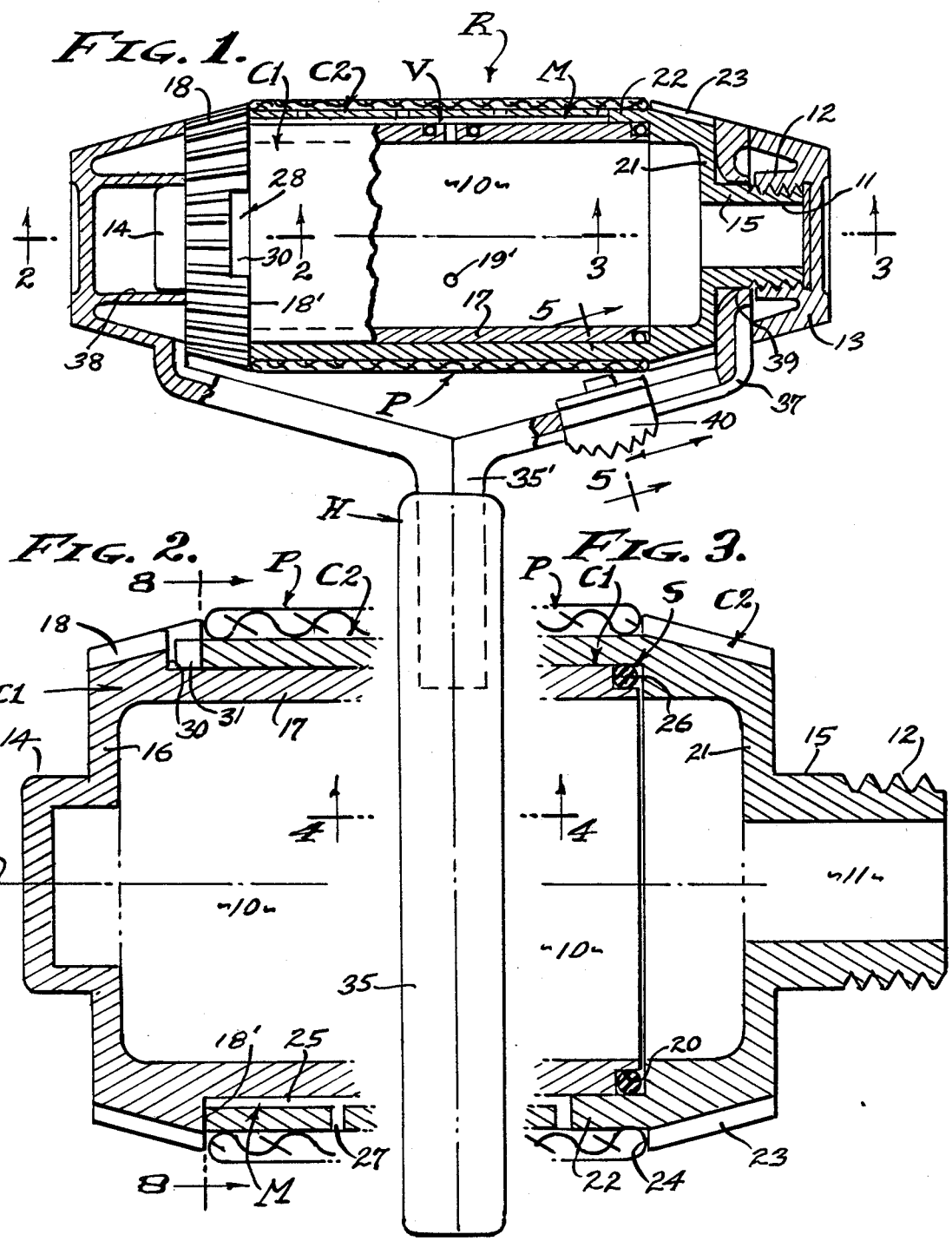

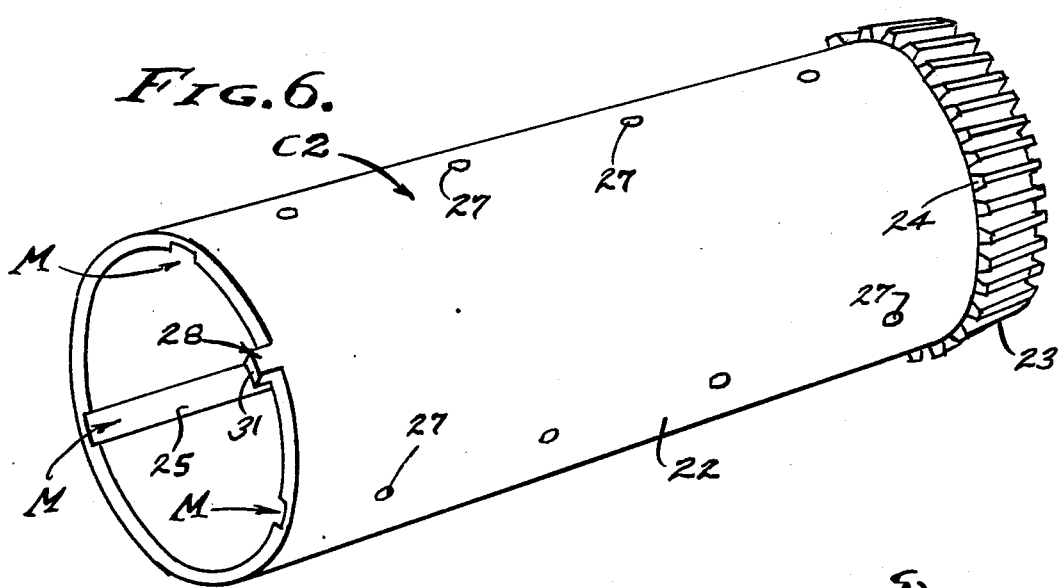
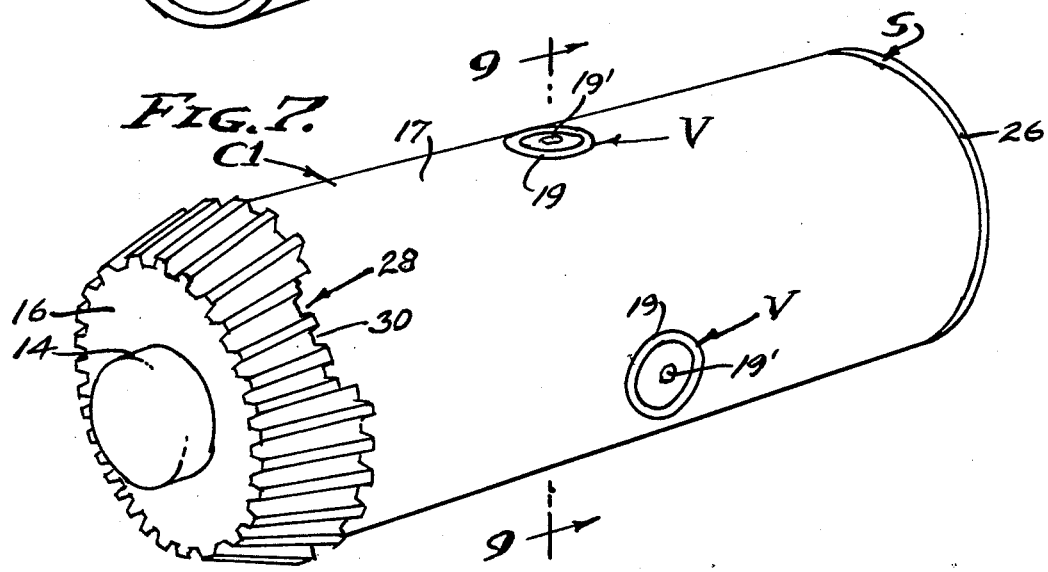
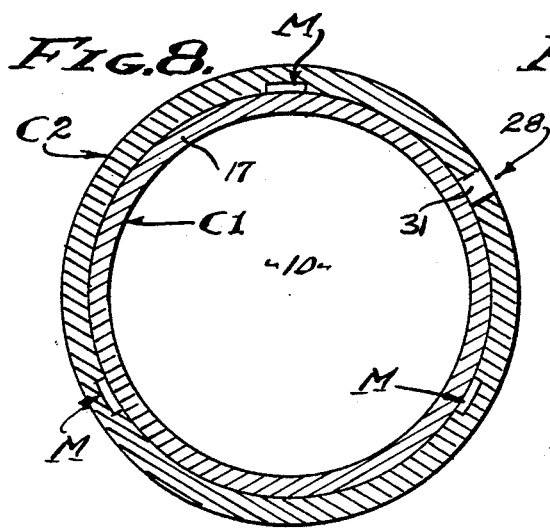
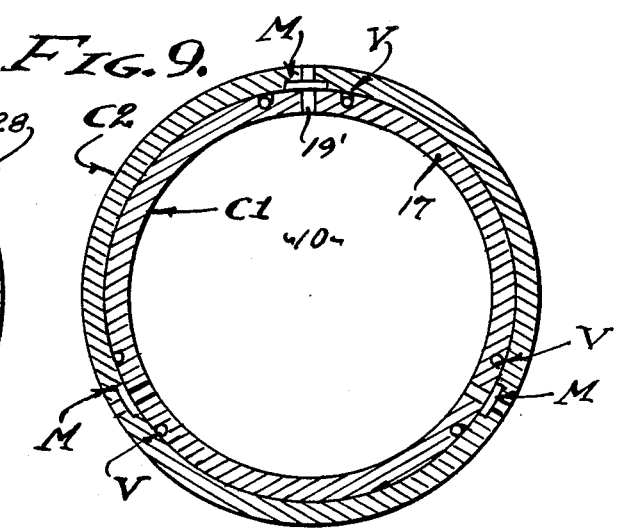

BODY ROLLER LIQUID APPLICATOR

BACKGROUND OF THE INVENTION

This invention relates to an applicator for applying liquids such as sun tan oil to a person's body, including the back of the body, and characterized by a roller which contains the liquid, and all of which is manipulated by a handle that provides an extension for access to one's back and for easy reach to the extremities of one's legs.

Heretofore, roller type applicators have been provided with a liquid supply through the handle, and fountain type painting devices involving rollers charged with a supply of paint have been available. However, the prior art devices have not provided the necessary simplicity and practicality suitable for the application of sun tan oils and the like. Therefore, it is a general object of this invention to provide a roller type applicator for applying oil and the like to one's body, wherein the oil is stored in the roller and is under a person's control for its descrete application. Accordingly, the roller is a liquid container having a replaceable closure, and is sectional for controlled manipulation of valve means incorporated therein for the discharge of said liquid. The liquid discharge is into an absorbent pad or sleeve that distributes the liquid throughout the peripheral surface of the roller for its application to body parts that are engaged thereby.

An object of this invention is to provide a liquid applicator of the type under consideration which is capable of being fabricated of the fewest number of injection molded plastic parts, and having the required functions. Firstly, the roller liquid container must be liquid tight when filled, it being an object of this invention to seal between sections of which the roller is constructed. Secondly, the roller liquid container must be valved to alternately store or discharge the liquid, it being an object of this invention to utilize restricted rotation of the roller sections with features incorporated therein as a valve. Thirdly, the discharge of liquid must be evenly distributed over the exterior of the roller, it being an object of this invention to provide manifolding within the roller sections for the uniform distribution of liquid into an absorbent pad or sleeve for application onto the body parts engaged thereby. Fourthly, the roller sections must be tightly assembled for both liquid storage and application, it being an object of this invention to utilize a handle which applies axial forces through opposite trunnion bearings which holds the roller sections assembled with pressure applied to seals. And fifthly, it may be desired that a scrubbing action be applied by the roller, it being an object of this invention that lock means prevent rotation of the roller when so required.

SUMMARY OF THE INVENTION

The liquid applicating roller as it is disclosed herein is fabricated of mating cylinder sections closed by a screw cap and with seals permitting restricted rotation for valve control. Discharge of liquid is distributed by manifolding to the roller exterior where it is absorbed into a pad or sleeve for subsequent application to a surface, in this particular application to a person's body parts. Application of liquid to otherwise inaccessible or inconvenient body parts is by means of an extended handle which also maintains axial assembly forces, final assembly being through deflection of the handle and its installation over bearing trunnions at opposite ends of the roller assembly. The two roller cylinders have restricted rotation for valve control. And, the entire roller assembly can be locked against rotation through switch means operable at the handle to engage with one of the roller cylinders.

The foregoing and various other objects and features of this invention will be apparent and fully understood from the following detailed description of the typical preferred forms and applications thereof, throughout which description reference is made to the accompanying drawings.

THE DRAWINGS

FIG. 1 is a side view of the assembly emdodying the device of the present invention, the top thereof being identified by the cap that closes the chamber therein that stores the liquid.

FIGS. 2 and 3 are enlarged sectional views taken as indicated by lines 2—2 and 3—3 on FIG. 1.

FIGS. 4 and 5 are enlarged detailed sectional views taken as indicated by line 4—4 and 5—5 on FIG. 1.

FIG. 6 is a perspective view of the outer cylinder section of the device.

FIG. 7 is a perspective view of the inner cylinder section of the device.

FIG. 8 is a sectional view taken through the bottom of the device as indicated by line 8—8 on FIG. 2.

And, FIG. 9 is sectional view taken through the inner cylinder section as indicated by line 9—9 on FIG. 7.

PREFERRED EMBODIMENT

Referring now to the drawings, FIG. 1 shows the assembled Body Roller Liquid Applicator, comprised generally of a roller R and a handle H for manipulation. The roller R is assembled of inner and outer cylinder sections C1 and C2 providing a liquid storage chamber 10 with a filler opening 11 in one of the cylinder sections and with a seal S between the cylinder sections. As shown, the filler opening 11 is through a neck 12 projecting from the outer cylinder section C2 and which is threaded to receive a screw cap closure 13 with a sealing gasket. Accordingly, the assembled cylinder sections C1 and C2 will contain and store liquid supplied through the neck 12. A feature is the restricted relative rotation of the cylinder sections and a valve means V incorporated therein to controllably discharge liquid through a manifold or manifolds M and into a pad or sleeve P for application to the parts of a person's body. Another feature is the removability of the handle H which permits replacement of the pad or sleeve P, and which is installed to maintain the device in operating condition.

FIGS. 2 and 3 of the drawings show the relationship of the cylinder sections C1 and C2 and as they are related to the handle H, whereby a fluid tight operable assembly is maintained. As shown, the two cylinder sections are coaxially disposed on an axis a, there being trunnions 14 and 15 projecting from opposite ends of the roller R, trunnion 14 from the inner cylinder section C1 and trunnion 15 from the outer cylinder section C2, to be rotatably carried in bearings of the handle H as later described. The two cylinder sections C1 and C2 are substantially coextensive, one telescopically rotatable over the other with means 28 restricting rotation of one with respect to the other (see FIGS. 7 and 8).

The inner cylinder section C1 (see FIGS. 2,3 and 7) has a bottom end wall 16 from which the trunnion 14 projects and from which a cylinder wall 17 projects to a top end wall of the other cylinder section C2 next described. A manually accessible rim 18 is provided at the perimeter of the wall 16 to form an inwardly faced shoulder 18' disposed in a plane normal to the rotational axis a. Shoulder 18' establishes a smooth sealing face to stop and seal against the bottom open end of the cylinder section C2 as next described. In accordance with this invention, the outer diameter surface of the cylinder wall 17 is provided with the valve means V for each of the manifolds M, there being three such manifolds shown (see FIG. 9) equally spaced circumferentially 120° apart. In practice, the valve means V is an "O" ring 19 seated in a recess in the outer surface of the cylinder wall 17 and surrounding an opening 19' from the chamber 10. In a closed condition the "O" ring $1_9$ seals with the inner diameter surface of the outer cylinder section C2 next described. The top end of cylinder section C1 is provided with a radially outward faced seat 20 for the seal S.

The outer cylinder section C2 (see FIGS. 2,3 and 6) has a top end wall 21 from which the trunnion 15 projects and from which a cylinder wall 22 projects to stop against the shoulder 19 of cylinder section C1. A manually accessible rim 23 is provided at the perimeter of the wall 21 forming an inwardly faced shoulder 24 disposed in a plane normal to the rotational axis a. Shoulder 24 is opposed to the shoulder 18' and between which the pad or sleeve P is engageably captured. The hereinabove described neck 12 extends through the trunnion 15 so as to open into the chamber 10, with the closure 13 accessible of the exterior of the assembly.

In accordance with this invention, the inner diameter surface of the cylinder wall 22 is provided with the manifold or manifolds M, each of which involves an axially disposed channel 25 coextensive with and opening at the inner diameter surface of the cylinder wall 22. However, the channel 25 stops short of the top end wall 21 so as to leave a smooth uninterrupted sealing wall opposed to the seat 20 at the open end of the cylinder section C1. In practice, the seal S is an "O" ring 26 confined between an axially faced should of seat 20 and the opposed face of top end wall 21, whereby the "O" ring is pressured to frictionally engage radially opposed sealing faces on the two cylinder sections C1 and C2. In an opened condition the "O" ring or "O" rings 19 align and register with the channel or channels 25 so that liquid from chamber 10 discharges into said channel or channels. In accordance with this invention, distribution by the manifold or manifolds M is through discharge ports 27 opening therefrom and to the outer diameter surface of the cylinder wall 22 and then into the body of the pad or sleeve P. In practice, there is a multiplicity of spaced ports 27 along the channel or channels 25.

Control of the valve means V is by a rotation limiting means 28 operating between the cylinder section C1 and C2 to positively stop them in either a valve open or a valve closed position. As shown, the rotation limiting means 28 is a circumferential notch 30 in the rim 18 of cylinder section C1 that is engaged by a lug 31 on the bottom open end of the cylinder section C2. The rotative motion permitted between the two cylinder sections restricts them to the two aforesaid positions. Referring now to the application of liquid, oil, discharge from chamber 10 and through the multiplicity of spaced distribution ports 27, the pad or sleeve P is a body of aborbent material slipped onto the outside diameter surface of the cylinder wall 22, and engaged between the shoulder 18' and shoulder 24, leaving the rims 18 and 23 exposed and accessible for manipulation and operation of the valve means V.

Referring now to the handle H, as shown in FIG. 1, there is a grip 35 from which there are oppositely extended arms 36 and 37 with opposed thrust bearings 38 and 39 that rotatably carry the trunnions 14 and 15 on the axis a. The arms 36 and 37 are flexible and of resilient material adapted to pressure the arms axially inward against the two cylinder sections C1 and C2. In practice, the bearings 38 and 39 are pressed by the arms to engage the bottom end and top end walls 16 and 21, so that the shoulder 18' of rim 18 forcibly engages the smooth bottom end face of the cylinder wall 22, so as to axially locate the cylinder section C1 within the cylinder section C2. This engagement prevents profuse discharge of liquid between rim 18 and the outer cylinder wall 22, and it simultaneously locates the top end of cylinder wall 17 juxtaposed to the top end wall 21 and properly compresses the "O" ring 26 of seal S. The resilient flexibility of the handle H permits its removal from and replacement over the trunnions of the two cylinder sections. As shown, the grip 35 is removable, for packaging, and secured to a central extension 35' of the arms 36 and 37. Alternately, the grip can be a telescoping member for compactness.

The lock means L prevents rotation of the roller R when so required for scrubbing and the like, and is shown herein as comprised of a switch 40 on the arm 37 to be manually positioned in and out of engagement with the rim 23 of cylinder section C2. In practice, the rims 18 and 23 are notched as shown for manual engagement, said notches being engageable by a projected end of the switch.

Having described only the typical preferred forms and applications of my invention, I do not wish to be limited or restricted to the specific details herein set forth, but wish to reserve to myself any modifications or variations that may appear to those skilled in the art, as set forth within the limits of the following claims.

I claim:

1. A body roller liquid applicator for storage and controlled discharge of liquid from its peripheral surface, and including;

inner and outer cylinder sections and one rotatably engaged coextensively over the other, the inner cylinder section having one end wall with a trunnion projecting therefrom on a turning axis and having a cylinder wall open at its other end, the outer cylinder section having one end wall with a trunnion projecting therefrom on said turning axis and having a cylinder wall open at its other end and rotatably receiving the cylinder wall of the inner cylinder section, a seal seated at said open other end of the inner cylinder section and at said one end wall of the outer cylinder section and confined therebetween establishing a closed storage chamber in the cylinder sections, there being an opening in the cylinder wall of the inner cylinder section and rotatable into alignment with a port in the cylinder wall of the outer cylinder section for controlled discharge of liquid, and a handle extension having bearings engaged over the trunnions with the cylinder sections rotatable therebetween.

2. The body roller liquid applicator as set forth in claim 1, wherein the seal at said open other end of the inner cylinder section at and said one end wall of the outer cylinder section is an "O" ring seal.

3. The body roller liquid applicator as set forth in claim 2, wherein a seat at the open end of the inner cylinder section confines the "O" ring seal both axially and radially, wherein the one end wall of the inner cylinder section is a bottom end wall and the one end wall of the outer cylinder section is a top end wall, wherein a filler opening extends through the trunnion at said top end wall and with a cap sealed thereto for filling access when the body roller liquid applicator is substantially erect, wherein a manually engageable flange is exposed radially at said one end wall of each cylinder section for manual engagement and relative rotation of said inner and outer cylinder section, and wherein a filler opening extends through said trunnion at the top end wall of the outer cylinder section.

4. The body roller liquid applicator as set forth in claim 1, wherein the seal at said open other end of the inner cylinder section and said one end wall of the outer cylinder section is an "O" ring seal, wherein a filler opening extends through one of said trunnions and with a cap sealed thereto for access outside the handle, wherein a sleeve of absorbent material slides over the outer cylinder section to receive the discharge of liquid and distribute the same coextensively over the periphery of the roller, and wherein relative rotation between the inner and outer cylinder sections is restricted to closed and open conditions of a valve means comprised of said opening and said port in the cylinder walls of the inner and outer cylinder sections.

5. The body roller liquid applicator as set forth in claim 1, wherein the one end wall of the inner cylinder section is a bottom end wall and the one end wall of the outer cylinder section is a top end wall, and wherein a filler opening extends through the trunnion at said top end wall with a cap sealed thereto for filling access when the body roller liquid applicator is substantially erect.

6. The body roller liquid applicator as set forth in claim 1, wherein a sleeve of absorbent material slides over the outer cylinder section to receive the discharge of liquid and distribute the same coextensively over the periphery of the roller.

7. The body roller liquid applicator as set forth in claim 1, wherein a manually engageable flange is exposed radially at said one end wall of each cylinder section for manual engagement and relative rotation of said inner and outer cylinder sections.

8. The body roller liquid applicator as set forth in claim 1, wherein a manually engageable flange is exposed radially at said one end wall of each cylinder section for manual engagement and relative rotation of said inner and outer cylinder sections, and wherein a sleeve of absorbent material slides over the outer cylinder section and between said flanges to receive the discharge of liquid and distribute the same coextensively thoughout the periphery of the roller.

9. The body roller liquid applicator as set forth in claim 1, wherein there is a plurality of longitudinally spaced discharge ports in the cylinder wall of the outer cylinder section, there being a channel opening at the inner diameter wall thereof to align with the opening in the cylinder wall of the inner cylinder section.

10. The body roller liquid applicator as set forth in claim 1, wherein a seal is seated in the outer diameter wall of the inner cylinder section and engaging the outer cylinder section surrounding the opening in the inner cylinder section.

11. The body roller liquid applicator a set forth in claim 1, wherein an "O" ring seal is seated in the outer diameter wall of the inner cylinder section and surrounding the opening therein.

12. The body roller liquid applicator as set forth in claim 1, wherein an "O" ring seal is seated in the outer diameter wall of the inner cylinder section and surrounding the opening therein, wherein there is a plurality of longitudinally spaced discharge ports in the cylinder wall of the outer cylinder' section, there being a channel opening at the inner diameter wall thereof to align with the opening in the cylinder wall of the inner cylinder section.

13. The body roller liquid applicator as set forth in claim 1, wherein relative rotation between the inner and outer cylinder sections is restricted to closed and open conditions of a valve means comprised of said opening and said port in the cylinder walls of the inner and outer cylinder sections.

* * * * *